US006369256B1

(12) United States Patent
Chi et al.

(10) Patent No.: US 6,369,256 B1
(45) Date of Patent: Apr. 9, 2002

(54) SELF-REDUCIBLE COPPER(II) SOURCE REAGENTS FOR CHEMICAL VAPOR DEPOSITION OF COPPER METAL

(75) Inventors: Yun Chi; Peng-Fu Hsu, both of Hsinchu; Tsung-Wu Lin; Chao-Shiuan Liu, both of Taipei, all of (TW); Arthur J. Carty, Ottawa (CA)

(73) Assignees: National Research Council of Canada (CA); National Tsing-Hua University (CN)

( * ) Notice: Subject to any disclaimer, the term of this patent is extended or adjusted under 35 U.S.C. 154(b) by 0 days.

(21) Appl. No.: 09/589,757

(22) Filed: Jun. 9, 2000

(51) Int. Cl.[7] .............................. C07F 1/08; C23C 16/18
(52) U.S. Cl. .................. 556/113; 427/250; 427/255.11; 427/593; 438/681
(58) Field of Search .................... 556/113; 427/593, 427/250, 255.11, FOR 101; 438/681

(56) References Cited

U.S. PATENT DOCUMENTS

| 3,356,527 A | 12/1967 | Moshier et al. ........... 117/107.2 |
| 5,084,201 A | * 1/1992 | Greco .................... 252/182.12 |
| 5,449,799 A | 9/1995 | Terfloth et al. ............. 556/112 |

FOREIGN PATENT DOCUMENTS

| EP | 1000948 | 5/2000 |

OTHER PUBLICATIONS

Chang et al., Canadian Journal of Chemistry, vol. 55, pp. 2465–2472 (1977).*

IN–Soon Chang et al: "Fluorinated Alkoxides. Part XI. Studies on Highly Fluorinated Amino–alcohols and their Metal Derivatives" Canadian Journal of Chemistry, vol. 55, No. 13, Jul. 1, 1977, pp. 265–2472, XP001024839, p. 2471, column 1, line 35—column 2, line 50.

* cited by examiner

Primary Examiner—Porfirio Nazario-Gonzalez
(74) Attorney, Agent, or Firm—J. Wayne Anderson

(57) ABSTRACT

Volatile low melting solid Cu(II) metal complexes are provided which are capable of depositing a copper film on various substrates under CVD conditions in the absence of reducing carrier gas $H_2$. These CU(II) metal complexes are represented by the structure formula:

$$Cu(OCCF_3R^1CH_2NHR^2)_2$$

wherein $R^1$ is selected from hydrogen, C1–C4 lower-alkyl or perfluorinated C1–C4 lower-alkyl groups, e.g., $CH_3$, and $CF_3$, etc., and wherein $R^2$ is C1–C6 lower-alkyl or C1–C6 lower-alkene, which may be substituted by one or more fluorine atoms, by a C1–C6 lower-alkoxy group or by a C1–C6 di-lower-alkyl amino group, provided that when $R^1$ is $CF_3$, $R^2$ is other than hydrogen or methyl. A process for depositing copper film using these Cu(II) metal complexes is also provided.

45 Claims, 1 Drawing Sheet

The molecular structure of IC6752; thermal ellipsoids drawn at the 30% probability level The molecular structure of IC6752; thermal ellipsoids drawn at the 30% probability level

SELF-REDUCIBLE COPPER(II) SOURCE REAGENTS FOR CHEMICAL VAPOR DEPOSITION OF COPPER METAL

BACKGROUND OF THE INVENTION

1. Field of the Invention

This invention relates to the preparation of a series of novel volatile Cu(II) metal complexes. The novel compounds, as well as some structurally similar known compounds can serve as precursors for high purity copper- or copper-containing thin-films in the absence of an external reducing reagent such as $H_2$, and to a method for the formation of copper- or copper-containing materials on substrites, such as silicon wafers for microelectronic devices, as well as for the generation of copper-containing which temperature superconducting ceramics.

Based on the need for Cu-based electric conductors, this art has sought improvements in source materials and deposition techniques for the formation of Cu metal thin-films.

Copper thin-film materials are of great interest for use as conducting layers in integrated circuits. More specifically, such materials have been utilized for manufacturing upper level metal interconnects and for filling contact and via holes. The advantages of copper over other possible conducting materials such as aluminum include: lower resistivity (1.7 $\mu\Omega$-cm for Cu, vs. 2.7 $\mu\Omega$-cm for Al); improved electromigration resistance (up to four orders of magnitude greater than Al) and increased resistance to stress-induced voidage (due to higher melting point vs. Al). There are also several well-known advantages related to device performance such as greater speed and reduced cross tall and smaller RC time constants.

2. Description of the Prior Art

Cu(HFac)$_2$, or copper (II) hexafluoroacetylacetonate, source reagents have been widely used to apply CVD copper to IC substrates and surfaces.[1] Copper thin films have also been prepared using the related air-stable β-acetoacetate and β-ketoimninate Cu(II) complexes.[2] The strategy for changing the ligand is either to increase the thermal stability and volatility, or to enhance the chance for selective deposition on different substrates and lower the deposition temperature of a Cu(II) complex. Upon introducing $H_2$ as an external reducing agent into the CVD system, relatively pure copper metal has been obtained at a much lower temperature. Under these experimental conditions, the reaction is best represented by the hydrogen reduction of a Cu(II) ion, which gives rise to the formation of free β-diketones as co-products:

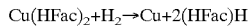

However, in the absence of an external reducing reagent, the above mentioned Cu(II) source reagents are notable for leaving large amounts of carbon, and other contaminates such as fluorine and oxygen in the deposited copper due to unwanted ligand decomposition. In addition, relatively high deposition temperatures must be used to decompose the source reagents into copper.

On the other hand, a second type or source reagent, involves the use of Cu(I) compounds to deposit copper thin film. The best known reagent of this kind is the complex (HFac)Cu(tmvs), wherein tmvs=trimethylvinylsilane,[3] that has been used as an industry standard to deposit copper by CVD. Other potentially suitable Cu(I) CVD source reagents involve (HFac)CuL, wherein L=phosphine ligands such as PMe$_3$ and PEt$_3$, alkyne ligands such as 2-butyne, and olefin ligands such as butadiene, 1,5-cyclooctadiene, 2-methyl-1-hexene-3-yne or other volatile organosilicon compounds containing unsaturated organic groups. These reagents have been used at low temperatures to deposit the required copper metal through a thermally induced disproportionation reaction, in the absence of reducing carrier gas, such as $H_2$. Using the Cu(J) complex (HFac)Cu(vtms) as an example, the reaction is best represented by the equation:

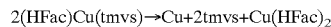

which involves the in-situ generation of deposited copper metal and a volatile Cu(II) complex Cu(HFac)$_2$ from a thermally induced disproportionation reaction. The film resistivity obtained with this source reagent is very good, approaching the physical limit of 1.7 $\mu\Omega$-cm, i.e. the resistivity of bulk copper. This suggests the formation of high quality copper thin film materials. However, the copper(I) complex (HFac)Cu(tmvs) becomes unstable and begins to decompose above 25° C. Thus, storage of this compound at around room temperature would lead to undesirable decomposition. In addition, the reagent (HFac)Cu(tmvs) must be converted from the liquid to the vapor state by heating during each CVD run. The aging and decomposition of (HFac)Cu(tmvs) would cause many unpredicted difficulties, such as extensive maintenance for the CVD instrument due to premature decomposition during vapor transport. In addition, this source reagent decomposes at relatively low temperature, which requires the use of lower temperatures for vapor transport and thus, lowers the precursor vapor pressure, resulting in a low rate for copper deposition, the formation of rough metal surfaces, and large variances in surface resistivity. Thus, many chemical additives and various precautions have been necessary to provide the precursors with a longer shelf life.

Accordingly, there is an urgent need for new CVD source reagents, possessing the advantages of both of the Cu(II) and Cu(I) source reagents mentioned above, namely: higher thermal and oxidative stability in air and at room temperature, lower melting point, higher vapor pressure under the designated CVD conditions;, and the capability of undergoing copper deposition in the absence of reducing carried gas $H_2$.

SUMMARY OF THE INVENTION

Thus, it is an object of the present invention to provide such CVD source reagents and a process for using these source reagents in the formation of the copper thin-films that are highly advantageous for integration with current CVD technologies. It is another object of the present invention to provide a simplified method to generate the required source reagents, and a rationale for synthesizing such reagents.

Other objects, features, and advantages will be more fully apparent from the ensuing disclosure and appended claims.

The present invention provides a series of novel Cu(II) metal complexes of the general formula:

wherein $R^1$ is hydrogen, C1–C4 lower-alkyl, C1–C4 perfluorinated lower-alkyl; and $R^2$ is C1–C6 lower-alkyl or C1–C6 lower-alkene, which may be substituted by one or more fluorine atoms, by a C1–C6 lower-alkoxy group or by a C1–C6 di-lower-alkyl amino group, provided that when $R^1$ is $CF_3$, $R^2$ is other than hydrogen or methyl. Specific examples of $R^2$ include: methyl, ethyl, allyl, n-propyl, i-propyl, 2-methoxyethyl, n-butyl, t-butyl, 3-methoxypropyl, 2,2,2-trifluoroethyl, 3,3,3,2,2-pentafluoro-n-propyl, $CH_2CH;NMe_2$, $CH_2CH_2CH_2NMe_2$ and $CH_2CH_2NEt_2$. It will be appreciated by those skilled in the art that, having established by example that $R^2$ may be a C1–C6 lower-alkoxy substituted alkyl, we can extrapolate $R^2$ to a C2–C3 di-lower-alkylamino substituent, because of the similar chemical behaviour of such groups.

The copper complexes of the present invention are readily synthesized by typical synthesis techniques using conventional procedures for forming the desired complexes. The most useful synthetic method involves the direct treatment of Cu(II) halide with an excess e.g. two equivalents of an alkali metal salt of the aminoalcohol ligand $HOCCF_3R^1CH_2NHR^2$ at elevated temperature in the range of 40 to 80° C., and using polar organic solvents such as THF, acetoine or diethyl ether as reaction media.

BRIEF DESCRIPTION OF THE DRAWING

The FIGURE is a three-dimensional illustration of a complex according to the invention.

DETAILED DESCRIPTION OF THE INVENTION

Figure 1:
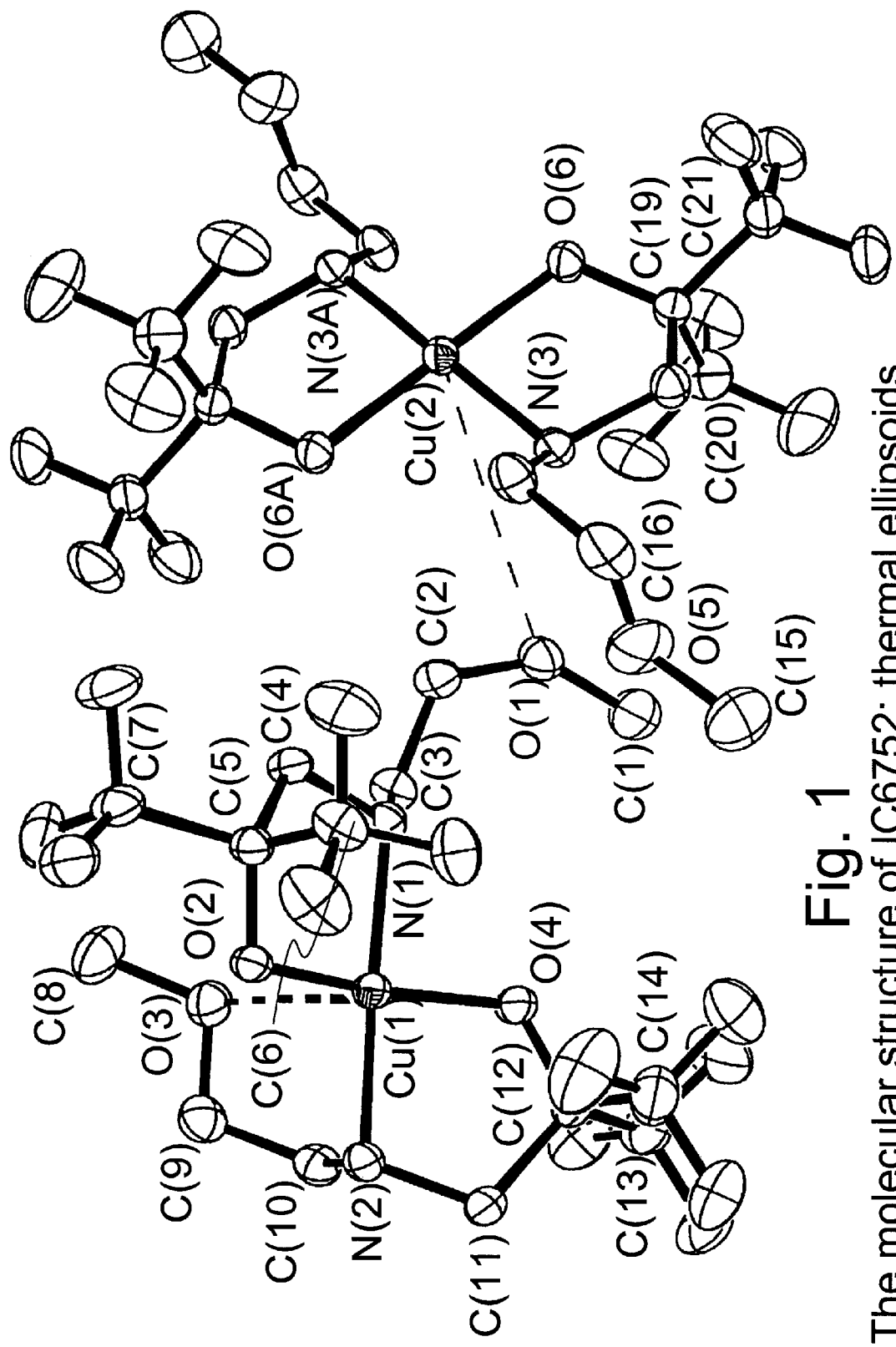

For the complexes containing at least one $CF_3$ substituent on the aminoalcohol ligand $HOCCF_3R^1 CH_2NHR^2$, a synthetic method according to the invention involves the direct treatment of Cu(II) halide complexes with two equivalents of an alkali metal salt of the aminoalcohol $HOCCF_3R^1CH_2NHR^2$ at elevated temperature, and using polar organic solvents such as THF, acetone or diethyl ether as reaction media. These chemical transformations are best represented by the following equation:

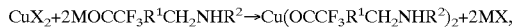

$$CuX_2+2MOCCF_3R^1CH_2NHR^2 \rightarrow Cu(OCCF_3R^1CH_2NHR^2)_2+2MX,$$

wherein X=halogen e.g. Cl or Br, and M=an alkali metal e.g. Li or Na.

This method is related to a method that has been used by Willis and coworkers in preparing two derivative complexes $Cu[OC(CF_3)_2CH_2NH_2]_2$ and $Cu[OC(CF_3)_2CH_2NHMe]_2$ which are structurally similar to the novel compounds according to this invention.[4] It is emphasized that although the structures of these compounds are known per se, there is no teaching or suggestion of the use of these complexes in CVD studies.

For structural identification, a single crystal X-ray diffraction study on the complex $Cu[OC(CF_3)_2 CH_2NHCH_2CH_2OMe]_2$ (1) has been carried out to confirm the exact structure. As indicated in FIG. 1, two crystallographical and structurally different molecules were observed within the crystallographic unit cell. In both molecules, the copper metal atom is surrounded by a square-planar arrangement involving two alkoxide oxygen and two amino nitrogen atoms located at the trans-disposition. The average Cu—N distance is 2.020 Å, which is longer than the average value of Cu—O distances 1.907 Å. However, the structures of these two molecules differ greatly from each other as the methoxyethyl substituents in one molecule reside on the same(cis) side of the $N_2O_2$ square, whereas the second molecule possesses a trans-arrangement for the methoxyethyl substituents.

Moreover, only the oxygen atom of the methoxyethyl pendents in the cis-isomer has been found to link with the Cu metal atom, which is indicated by two slightly longer non-bonding contacts. One of these is the intramolecular bonding Cu(1)—O(3)=2.628 Å while the second forms the intermolecular interaction Cu(2)—O(1)=3.874 Å. This result is in contrast to that reported for the related Cu(II) complex $Cu(hfac)_2H_2O$,[5] of which the strongly bonded water solvate is located at the axial site, with Cu—O($H_2O$)= 2.204(3) Å. For the second type of Cu(II) complex such as $Cu[OC(CF_3)_2CH_2NHCH_2CH=CH_2]_2$ (2), which does not possess the pendent methoxyethyl group, an X-ray diffraction study shows that the molecular structure adapts the all trans-disposition for the $N_2O_2$ square framework and for the allyl substituent of both amino fragments.

All other synthesized Cu(II) source complexes are readily characterized by mass spectrometry (MS), elemental analysis, and thermal gravimetric analysis (TGA). Selected physical properties of these Cu(II) source reagents of the present invention are summarized in Table 1.

TABLE 1

Physical properties of the Cu(II) source reagents of the present invention

| Entry | Compound | M. P. (° C.) | Dec. (° C.) | $T_{1/2}$ (° C.)[a] | % Residue[b] | Remarks |
|---|---|---|---|---|---|---|
| 1 | $Cu[OC(CF_3)_2CH_2NHCH_2CH_2OMe]_2$ | 87–88 | 170 | 179 | 0.6 | |
| 2 | $Cu[OC(CF_3)_2CH_2N(CH_2CH_2OMe)_2]_2$ | 88–89 | 233 | 230 | 0.5 | |
| 3 | $Cu[OC(CF_3)_2CH_2NHCH_2CH=CH_2]_2$ | 123–124 | 170 | 165 | 2.0 | |
| 4 | $Cu[OC(CF_3)_2CH_2N(CH_2CH=CH_2)_2]_2$ | 128–129 | 179 | 191 | 7.9 | |
| 5 | $Cu[OC(CF_3)_2CH_2NHPr^n]_2$ | 133–134 | 165 | 161 | 2.1 | |
| 6 | $Cu[OC(CF_3)_2CH_2NHBu^n]_2$ | 106–107 | 161 | 175 | 1.1 | |
| 7 | $Cu[OC(CF_3)_2CH_2NHBu^i]_2$ | 120–121 | 159 | 154 | 1.0 | |
| 8 | $Cu[OC(CF_3)_2CH_2NHBu^i]_2$ | 167–168 | 202 | 184 | 3.5 | |
| 9 | $Cu[OC(CF_3)_2CH_2NHMe]_2$ | 204–205 | 200 | 184 | 0.7 | |
| 10 | $Cu[OC(CF_3)_2CH_2NH_2]_2$ | ≧dec.[c] | 280 | 282 | 13.5 | in-volatile |
| 11 | $Cu[OCMe(CF_3)CH_2NHCH_2CH_2OMe]_2$ | 151–152 | 175 | 179 | 9.9 | |
| 12 | $Cu[OCMe(CF_3)CH_2NHCH_2CH=CH_2]_2$ | ≧dec.[c] | 196 | 193 | 20.4 | |
| 13 | $Cu[OCMe(CF_3)CH_2NHBu^n]_2$ | ≧dec.[c] | 183 | 194 | 10.6 | |
| 14 | $Cu[OCMe(CF_3)CH_2NH(CH_2)_5Me]_2$ | 147–148 | 185 | 180 | 11.1 | |
| 15 | $Cu[OCMe(CF_3)CH_2NHPr^i]_2$ | ≧dec.[c] | 181 | 184 | 8.3 | |
| 16 | $Cu[OCMe(CF_3)CH_2NHCHEt_2]_2$ | 109–110 | 180 | 161 | 8.4 | |
| 17 | $Cu[OCMe(CF_3)CH_2NHBu^i]_2$ | 165–166 | 174 | 173 | 7.5 | |
| 18 | $Cu[OCMe(CF_3)CH_2NHCMe_2Et]_2$ | 71–72 | 170 | 162 | 10.0 | |
| 19 | $Cu[OCH(CF_3)CH_2NHCH_2CH_2OMe]_2$ | 116–117 | 200 | 193 | 13.9 | |
| 20 | $Cu[OCH(CF_3)CH_2N(CH_2CH_2OMe)_2]_2$ | 122–123 | 181 | 236 | 8.9 | |
| 21 | $Cu[OCH(CF_3)CH_2NHPr^n]_2$ | ≧dec.[c] | 203 | 200 | 14.8 | |

TABLE 1-continued

Physical properties of the Cu(II) source reagents of the present invention

| Entry | Compound | M. P. (° C.) | Dec. (° C.) | $T_{1/2}$ (° C.)[a] | % Residue[b] | Remarks |
|---|---|---|---|---|---|---|
| 22 | $Cu[OCH(CF_3)CH_2NPr^n{}_2]_2$ | 74–75 | 193 | 204 | 2.0 | |
| 23 | $Cu[OCH(CF_3)CH_2NHBu^i]_2$ | ≧dec.[c] | 158 | 167 | 18.1 | |

[a]The temperature at which 50 wt. % of the sample has been lost during TGA analysis (heating rate = 10° C./min and $N_2$ flow rate = 100 cm$^3$/min).
[b]Total weight percent of the sample observed at 500° C. during TGA analysis.
[c]Melting-point is greater than decomposition temperature.

According to the physical data listed in Table 1, it appears that the air stability and the volatility are proportional to the number of the $CF_3$ substituents attached to the aminoalcoholate ligands. For example, the complexes $Cu[OCH_2CH_2NMe_2]_2$ and $Cu[OCMe_2CH_2NHPr^n]_2$ do not possess any $CF_3$ substituent; as a result, they are highly air-sensitive and decomposes readily upon exposure to air at room temperature. For the complexes (11~18) that possess only one $CF_3$ substituent, these are stable against moisture and oxygen in air, thus they can be stored at room temperature for over a long period. However, they are not so volatile as indicated by the slightly higher melting points, the greater $T_{1/2}$ values and the greater residual weight percent obtained in the TGA study. The complexes 12, 13 and 15 start to decompose before there are any signs of melting, suggesting that their melting points are much higher than the onset temperature for sample decomposition.

Furthermore, the Cu(II) complexes (1~9) which possess two $CF_3$ groups, i.e. $R^1=CF_3$, have the greatest volatility and stability and has been clearly indicated by observation of lower melting points, lower $T_{1/2}$ values and smaller residual weights percent in the TGA data, We believe that the low polarizability of the perfluorinated alkyl substituents that reduced the intermolecular attractive interaction is the key factor for the enhancement of volatility.[6] On the other hand, the high electronegativity of the fluorinated alkyl groups would reduce the basicity of the alkoxy oxygen, which would lead to an increase of the formal positive charge on the Cu(II) metal center and, in turn, improves the strength of the amine to Cu(II) ion dative bonding. This electronic effect makes the complexes 1~9 (with two $CF_3$ groups) more stable than the other complexes 11~18 (possessing only one $CF_3$ group), which are in turn more stable than the complexes such as $Cu[OCH_2CH_2NMe_2]_2$ and $Cu[OCMe_2CH_2NHPr^n]_2$ which do not have a $CF_3$ group. As a result, these $CF_3$-containing compounds (1~9 and 11~18) should be more suitable for CVD of copper metal.

In addition, the nature of the amino functional group within the aminoalcoholate ligand also has a significant influence on the chemical as well as the physical properties. For example, the prior art complex 10 possesses a primary amino functional group on the aminoalcoholate ligand. Our experimental observation shows that this complex cannot be sublimed under vacuum (200 mtorr, 150° C.) and possesses the highest $T_{1/2}$ value for all complexes recorded (282° C.); therefore, it is a poor source reagent for CVD investigation. Furthermore, both complexes 2 and 4 show the occurrence of a 3° amino functional group on the aminoalcoholate ligands. Interestingly, they also exhibit higher $T_{1/2}$ data with respect to their counterparts 1 and 3, which instead possess a more reactive 2° amino functional group. In agreement with this finding, further investigation of their physical data suggests that the complexes 2 and 4 are slightly less volatile and more stable. The latter property is caused by the lack of a lower energy pathway for decomposition. Therefore, these complexes require a higher temperature for depositing copper metal, making them unsuitable CVD source reagents due to the uncontrollable ligand decomposition that occurs at higher deposition temperatures.

For complexes which possess the 2° amino functional groups, the lower energy decomposition pathway may involve the self-catalyzed intramolecular dehydrogenation of 2° amine, giving formation of an imino fragment on one of the chelated aminoalcoholate ligands. The hydrogen atoms released from this dehydrogenation process would then transfer to both the alcoholate termini, giving a 1:1 mixture of iminoalcohol and aminoalcohol:[7]

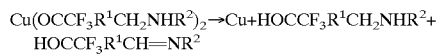

Such postulation is supported by the facile oxidation of 2° amines with the Cu(II) reagent in THF solution at room temperature, of which the Cu(II) oxidant is in-situ generated from mixing equal amount of $CuBr_2$ and $LiOBu^t$ prior to the reaction.[8] Alternatively, the second pathway involves formation of a ketone, an imine fragment and the corresponding aminoalcohol according to the equation listed below:

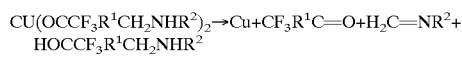

The ketone and the imine are formed by a $C(\alpha)$-$C(\beta)$ bond fission reaction and a co-operative hydrogen transfer from the nitrogen atom of one aminoalcoholate to the oxygen atom of the second and, concurrently, the central Cu(II) ion is reduced to the metallic state. This proposed reaction sequence is not completely unprecedented, as oxidation of the β-aminoalcohols in solution by electrochemical means has afforded the related imine intermediate and the ketone product by cleavage of the carbon-carbon bond between the hydroxyl and the amine functional groups.[9] In support of this postulation, the NMR and GC-MS studies show that the condensable products collected during CVD runs contains large amount of hexafluoroacetone, $H_2NBu^t$ and a 1,3-oxazolidine compound ($R^1=CF_3$, $R^2=Bu^t$) from the CVD experiment using the source complex $Cu[OC(CF_3)_2CH_2NHBu^t]_2$ (8). According to the data reported in literature,[10] the 1,3-oxazolidine is possibly obtained from a secondary, cyclization reaction between the imine $H_2C=NR^2$ and the dissociated aminoalcohol ligand.

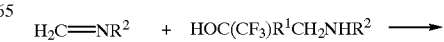

-continued

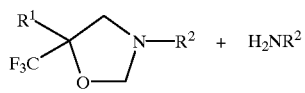

The same 1,3-oxazolidine is also detected as the major product from the direct treatment of the β-aminoalcohol HOC(CF$_3$)$_2$CH$_2$NHBu$^1$ with iodosobenzene, which has been applied as a standard oxidant for preparation of both aromatic and aliphatic imines from 2° amines.[11]

Finally, as complex 1 possesses the lowest melting point 87–88° C., it has the potential to serve as a liquid precursor which has an advantage for having table rate of vapor transport, under conditions where the temperature of reservoir is raised above the melting point. We speculate that the observed decrease in melting point is caused by the methoxyethyl substituents within the molecule, The formation of many inter- and intramolecular Cu—O interactions within the sample has the notable effect of weakening the adjacent Cu—N dative bonds, which then further facilitate the cis- and trans-isomerization at the —NHCH$_2$CH$_2$OMe fragments. The result of an X-ray structural determination is in good agreement with this hypothesis, showing the coexistence of both cis- mid trans-isomers in a 1:1 ratio, and the association of inter- and intramolecular Cu—O interactions.

In another aspect, the invention relates to the use of the Cu(II) complexes of the general formula: Cu(OCCF$_3$R$^1$CH$_2$NHR$^2$)$_2$ as source reagents for CVD applications. In general, the Cu(II) reagent is first placed in a source reservoir of a CVD reactor, then it may be volatilized by heating to yield a copper metal source vapor, and the source vapor may be contacted with a substrate in the CVD reactor, allowing deposition of copper. Examples of the substrate materials include: pyrex glass, Si wafer and titanium nitride thin films. Preferably, the source reservoir is maintained at about 80–160° C. to give an optimal vapor pressure, while the reaction chamber is maintained at about 250–400° C. during the deposition process, and more preferably about 250–300° C. Deposition of copper was carried out in the absence of carrier gas, and using Ar or H$_2$ as the carrier gas to facilitate vapor transport. The source reagents and the run conditions selected for the CVD experiments, and the basic properties of the copper films produced are summarized in Table 2.

Based on the data summarized in Tables 1 and 2, we may conclude that the Cu(II) source reagents mentioned in this invention comprise the following advantages:

Higher thermal and oxidative stability in air. Most of the Cu(II) source reagents containing at least one CF$_3$ substituent can be handled in air at room temperature without showing significant decomposition.

Possibility of serving as a liquid CVD precursor. Complex 1, which shows a relatively lower melting point at below 88° C., can be used as a liquid precursor if the reservoir temperature is kept above its melting point.

Enhanced vapor pressure under the designated CVD conditions. Most of the Cu(II) source reagents can be sublimed without showing significant decomposition at around 300 mtorr and at a temperature below 120° C.

Capability of undergoing copper deposition at lower temperature vs. other Cu(II) reagents, such as Cu(HFac)$_2$, and in the absence of reducing carrier gas H$_2$. For example, using no carrier gas or employing a slow stream of inert carrier gas such as Ar, complex 17 gives a copper film with purity greater than 99% at a deposition temperature of 250° C. On the other hand, the introduction of a reducing carrier gas such as H$_2$ shows very little (or no significant) improvement, suggesting that the ligands of these complexes have already provided the essential reducing power for deposition of Cu thin-film.

Although our analytical data indicated that the purity of Cu films obtained in our study is not quite 100% pure, we believe that the quality of the Cu films can be further improved by changing and upgrading the design of the CVD apparatus.

EXPERIMENTAL SECTION

Without intending to limit it in any manner, the present invention will be further illustrated by the following examples.

EXAMPLE 1

Synthesis of Cu[OC(CF$_3$)$_2$CH$_2$NHCH$_2$CH$_2$OMe]$_2$

Sodium hydride (0.151 g, 6 mmol) was suspended in 25 mL of THF. To this was added dropwise 1.26 g of the aminoalcohol ligand HOC(CF$_3$)$_2$CH$_2$NHCH$_2$CH$_2$OMe (5 mmol) in THF (25 mL). The mixture was further stirred for 2 hours until evolution of gas has ceased. After then, the

TABLE 2

Data obtained from CVD experiment using the Cu(II) aminoalcoholate complexes as source reagents and pyrex glass, Si wafer and titanium nitride as substrates

| Compound | Carrier Gas F.R. (mL/min) | Source Temp. (° C.) | Substrate Temp. (° C.) | Deposition Rate (Å/min) | Film Compositions and Conductivity ρ(μΩ-cm) |
|---|---|---|---|---|---|
| 1 | None | 140 | 250 | 190 | Cu, 97%; C, 0.6%; O, 1.1%; F, 1.0%. ρ = 12.4. |
| 1 | None | 140 | 300 | 140 | Cu, 97%; C, 0.6%; O, 1.4%; F, 1.1%. ρ = 11.8. |
| 1 | H$_2$ (25) | 140 | 250 | 75 | Cu, 96%; C, 1.2%; O, 1.1%; F, 1.7%. |
| 1 | H$_2$ (25) | 140 | 300 | 60 | Cu, 97%; C, 1.0%; O, 1.1%; F, 1.2%. |
| 8 | Ar (10) | 150 | 250 | 110 | Cu, 97%; C, 0.3%; O, 1.7%; F, 1.2%. ρ = 4.02. |
| 8 | Ar (10) | 150 | 275 | 200 | Cu, 97%; C, 0.3%; O, 1.9%; F, 1.1%. ρ = 2.65. |
| 17 | Ar (35) | 155 | 250 | 135 | Cu, 99.2%; C, 0.0%; O, 0.7%; N, 0.1%. ρ = 3.44. |
| 17 | Ar (35) | 155 | 275 | 174 | Cu, 99.3%; C, 0.0%; O, 0.6%; N, 0.1%. ρ = 6.45. |
| 17 | Ar (35) | 155 | 300 | 185 | Cu, 94.2%; C, 4.2%; O, 1.0%; N, 0.6%. ρ = 401.3. |
| 17 | Ar (35) | 155 | 325 | 190 | Cu, 94.4%; C, 4.4%; O, 0.7%; N, 0.5%; ρ = 3875. |
| 17 | H$_2$ (25) | 155 | 250 | 137 | Cu, 98.6%; C, 0.3%; O, 0.9%; N, 0.2%. ρ = 4.27. |
| 17 | H$_2$ (25) | 155 | 275 | 242 | Cu, 99.9%; C, 0%; O, 0.1%; N, 0%. ρ = 3.36. |
| 17 | H$_2$ (25) | 155 | 300 | 212 | Cu, 98.6%; C, 0.7%; O, 0.5%; N, 0.2%. ρ = 14.07. | filtrate was transferred into a 100 mL reaction flask containing a suspension of $CuCl_2$ (0.40 g, 3 mmol) in THF solution (25 mL). This mixture was first stirred at room temperature for 4 hours giving a purple homogeneous solution alone with an off-white NaCl precipitate. The precipitate was then removed by filtration, the filtrate was concentrated to dryness, and the resulting residue was purified by vacuum sublimation (193 mtorr, 72° C.), giving 1.20 g of purple copper complex $Cu[OC(CF_3)_2CH_2NHCH_2CH_2OMe]_2$ (2.1 mmol, 84%). Crystals of $Cu[OC(CF_3)_2CH_2NHCH_2CH_2OMe]_2$ suitable for single crystal X-ray diffraction study were grown from a mixed solution of $CH_2Cl_2$ and hexane at room temperature.

Spectral data of $Cu[OC(CF_3)_2CH_2NHCH_2CH_2OMe]_2$: MS (EI, 70 eV, m/e$^+$, L=$C_7H_{10}F_6NO_2$), observed (actual) [assignment] {relative intensity}: 571 (571) [CuL$_2$] {3.14}, 502 (502) [CuL$_2$—CF$_3$] {1.86}, 405 (405) [CuL$_2$—C$_3$F$_6$O] {17.50}, 3.18 (317) [CuL] {100.00}, 254 (254) [L] {10.86}, 150 (151) [CuL—C$_3$F$_6$O] {59.69}, 88 (88) [L—C$_3$F$_6$O] {20.63}. Anal. Calcd for $C_{14}H_{20}F_{12}N_2O_4Cu$: C, 29.40, H, 3.53; N,4.90. Found: C, 29.49; H, 3.98; N, 5.27.

EXAMPLE 2

Synthesis of $Cu[OC(CF_3)_2CH_2NHCH_2CH=CH_2]_2$

The procedures of Example 1 were followed, using 0.15 g of sodium hydride (6 mmol), 1.19 g of the aminoalcohol ligand $HOC(CF_3)_2CH_2NHCH_2CH=CH_2$ (5 mmol) and 0.40 g of $CuCl_2$ (3 mmol). After removing the THF solvent, vacuum sublimation (254 mtorr, 78° C.) gave purple solid $Cu[OC(CF_3)_2CH_2NHCH_2CH=CH_2]_2$ (1.12 g, 2.1 mmol) in 83% yield. Crystals suitable for single crystal X-ray diffraction study were grown from a nixed solution of $CH_2Cl_2$ and hexane at room temperature.

Spectral data of $Cu[OC(CF_3)_2CH_2NHCH_2CH=CH_2]_2$: MS (EI, 70 eV, m/e$^+$, L=$C_7H_8F_6NO$), observed (actual) [assignment] {relative intensity}: 598 (598) [CuL$_2$+Cu] {8.71}, 535 (535) [CuL$_2$] {12.63}, 369 (369) [CuL$_2$—C$_3$F$_6$O] {18.18}, 300 (299) [CuL] {76.77}, 236 (236) [L] {31.31}, 132 (133) [CuL—C$_3$F$_6$O] {69.19}, 70 (70)[L—C$_3$F$_6$O] {100.00}, 69 (69) [CF$_3$] {7.86}. Anal. Calcd for $C_{14}H_{16}F_{12}N_2O_2Cu$; C, 31.38; H, 3.01; N, 5.23. Found: C, 31.44; H, 3.08; N, 5.25.

EXAMPLE 3

Synthesis of $Cu[OC(CF_3)_2CH_2NHBu^n]_2$

The procedures of Example 1 were followed, using 0.15 g of sodium hydride (6 mmol), 1.26 g of the aminoalcohol ligand $HOC(CF_3)_2CH_2NHBu^n$ (5 mmol) and 0.40 g of $CuCl_2$ (3 mmol). After removing the THF solvent, vacuum sublimation (192 mtorr, 68° C.) gave purple solid $Cu[OC(CF_3)_2CH_2NHBu^n]_2$ (1.20 g, 2.1 mmol) in 83% yield.

Spectral data of $Cu[OC(CF_3)_2CH_2NHBu^n]_2$: MS (EI, 70 eV, m/e$^+$L=$C_8H_{12}F_6NO$), observed (actual) [assignment] {relative intensity}: 630 (630) [CuL$_2$+Cu] {9.35}, 567 (567) [CuL$_2$] {21.85}, 401 (401) [CuL$_2$—C$_3$F$_6$O] {72.97}, 331 (332) [CuL$_2$—C$_3$F$_6$O—CF$_3$] {5.21}, 316 (315) [CuL] {58.56}, 252 (252) [L]{49.10}, 182 (183) [L—CF$_3$] {5.49}, 148 (149) [CuL—C$_{3F_6}$O] {93.24}, 92 (91) [CuL—C$_3$F$_6$O—C$_4$H$_9$] {6.90}, 86 (86) [L—C$_3$F$_6$O] {100.00}, 57 (57) [C$_4$H$_9$] {6.33}. Anal. Calcd for $C_{16}H_{24}F_{12}N_2O_2Cu$: C, 33.84; H, 4.26; N, 4.93. Found. C, 33.78; H, 4.21; N, 4.97.

EXAMPLE 4

Synthesis of $Cu[OC(CF_3)_2CH_2NHPr^n]_2$

The procedures of Example 1 were followed, using 0.15 g of sodium hydride (6 mmol), 1.20 g of the aminoalcohol ligand $HOC(CF_3)_2CH_2NHPr^n$ (5 mmol) and 0.40 g of $CuCl_2$ (3 mmol). After removing the THF solvent, vacuum sublimation (178 mtorr, 60° C.) gave purple solid $Cu[OC(CF_3)_2CH_2NHPr^n]_2$ (1.08 g, 2.0 mmol) in 81% yield.

Spectral data of $Cu[OC(CF_3)_2CH_2NHPr^n]_2$: MS (EI, 70 eV, m/e$^+$; L=$C_7H_{10}F_6NO$), observed (actual) [assignment] {relative intensity}: 602 (602) [CuL$_2$+Cu] {5.76}, 539 (539) [CuL$_2$] {19.13}, 373 (373) [CuL$_2$—C$_3$F$_6$O] {38.55}, 303 (304) [CuL$_2$—C$_3$F$_6$O—CF$_3$] {7.42}, 302 (301) [CuL] {42.77}, 238 (238) [L] {36.60}, 168 (169) [L—CF$_3$] {5.87}, 134 (135) [CuL—C$_3$F$_6$O] {51.81}, 92 (92) [CuL—C$_3$F$_6$O—C$_3$H$_7$]{5.01},72 (72) [L—C$_3$F$_6$O] {100.00}, 69 (69) [C$_3$H$_7$] {5.31}. Anal. Calcd for $C_{14}H_{20}F_{12}N_2O_2Cu$: C, 31.15; H, 3.73; N, 5.19. Found: C, 31.23; H, 3.70; N, 5.12.

EXAMPLE 5

Synthesis of $Cu[OC(CF_3)_2CH_2NHBu^i]_2$

The procedures of Example 1 were followed, using 0.15 g of sodium hydride (6 mmol), 1.26 g of the aminoalcohol ligand $HOC(CF_3)_2CH_2NHBu^i$ (5 mmol) and 0.40 g of $CuCl_2$ (3 mmol). After removing the THF solvent, vacuum sublimation (202 mtorr, 68° C.) gave purple solid $Cu[OC(CF_3)_2CH_2NHBu^i]_2$ (1.12 g. 2.0 mmol) in 79% yield.

Spectral data of $Cu[OC(CF_3)_2CH_2NHBu^i_2$: MS (EI, 70 eV, m/e$^+$. L=$C_8H_{12}F_2NO$), observed (actual) [assignment] {relative intensity}: 567 (567) [CuL$_2$] {14.69}, 401 (401) [CuL$_2$—C$_3$F$_6$O] {43.83}, 316 (315) [CuL$_2$—L] {48.70}, 252 (252) [L] {29.22}, 148 (149) [CuL—C$_3$F$_6$O] {50.32}, 86 (86) [L—C$_3$F$_6$O] {100.00}, 69 (69) [CF$_3$] {9.90}, 57 (57) [C$_4$H$_9$] {12.66}. Anal. Calcd for $C_{16}H_{24}F_{12}N_2O_2Cu$: C, 33.84; H, 4.26; N, 4.93. Found: C, 32.92; H,4.37; N, 4.96.

EXAMPLE 6

Synthesis of $Cu[OC(CF_3)_2CH_2NHMe]_2$

The procedures of Example 1 were followed, using 0.15 g of sodium hydride (6 mmol), 1.06 g of the aminoalcohol ligand $HOC(CF_3)_2CH_2NHMe$ (5 mmol) and 0.40 g of $CuCl_2$ (3 mmol). After removing the THF solvent, vacuum sublimation (232 mtorr, 82° C.) gave purple solid $Cu[OC(CF_3)_2CH_2NHMe]_2$ (0.82 g, 2.0 mmol) in 68% yield.

Spectral data of $Cu[OC(CF_3)_2CH_2NHMe]_2$: MS (EI, 70 eV, m/e$^+$. L=$CH_6F_6NO$), observed (actual) [assignment] {relative intensity} 483 (483) [CuL$_2$] {10.63}, 414 (414) [CUL$_2$—CF$_3$] {5.69}, 317 (317) [CuL$_2$—C$_3$F$_6$O] {68.86}, 274 (273) [CuL] {52.10}, 210 (210) [L] {52.10}, 149 (151) [CuL$_2$—2(C$_3$F$_6$O)] {25.60}, 140 (141) [L—CF$_3$] {5.16}, 106 (107) [CuL—C$_3$F$_6$O] {100.00}, 97 (97) [C$_3$F$_6$O—CF$_3$] {6.62}, 69 (69) [CF$_3$] {11.38}. Anal. Calcd for $C_{10}H_{12}F_{12}N_2O_2Cu$: C, 24.83, H, 2.50; N, 5.79. Found: C, 24.84; H, 2.75; N, 5.79.

EXAMPLE 7

Synthesis of $Cu[OC(CF_3)_2CH_2NH_2]_2$

The procedures of Example 1 were followed, using 0.15 g of sodium hydride (6 mmol), 1.06 g of the aminoalcohol ligand $HOC(CF_3)_2CHN_2$ (5 mmol) and 0.40 g of $CuCl_2$ (3 mmol). After stirring the mixture at RT for 4 hours, the NaCl precipitate was removed by filtration, the filtrate was concentrated to dryness, and the residue was purified by crystallization, giving 0.26 g of purple complex $Cu[OC(CF_3)_2CH_2NH_2]_2$ (0.6 mmol, 23%). Crystals suitable for single crystal X-ray diffraction study were grown from THF solution at room temperature.

Spectral data of $CU[OC(CF_3)_2CH_2NH_2]_2$: MS (FAB, m/e$^+$, L=$C_4H_4F_6NO$), observed (actual) [assignment]: 455, (455) [CuL$_2$]. Anal. Calcd for $C_8H_8F_{12}N_2O_2Cu$: C, 21.09; H, 1.77; N, 6.15. Found: C, 20.96; H, 1.75; N, 6.41.

EXAMPLE 8

Synthesis of $Cu[OCMe(CF_3)CH_2NHCH_2CH_2OMe]_2$

The procedures of Example 1 were followed, using 0.19 g of sodium hydride (7.5 mmol), 1.01 g of the aminoalcohol ligand $HOCMe(CF_3)CH_2NHCH_2CH_2OMe$ (5 mmol) and 0.27 g of $CuCl_2$ (2 mmol). After removing the THF solvent, vacuum sublimation (23 mtorr, 90° C.) gave purple solid $Cu[OCMe(CF_3)CH_2NHCH_2CH_2OMe]_2$ (0.57 g, 1.24 mmol) in 62% yield.

Spectral data of $Cu[OCMe(CF_3)CH_2NHCH_2CH_2OMe]_2$: MS (EI, 70 eV, m/e$^+$, L=$C_7H_{13}F_3NO_2$), observed (actual) [assignment] {relative intensity}: 463 (463) [CuL$_2$] {3.72}, 394 (394) [CuL$_2$—CF$_3$] {0.60}, 351 (351) [CuL$_2$—C$_3$F$_3$H$_3$O] {4.08}, 264 (263) [CuL] {70.22}, 150 (151) [CuL—C$_3$F$_3$H$_3$O] {7.33}, 88 (88) [L—C$_3$F$_3$H$_3$O] {100}. Anal. Calcd for $C_{14}H_{26}F_6N_2O_4Cu$: C, 36.25; H, 5.65; N, 6.04. Found: C, 36.23; H, 5.85; N, 6.16.

EXAMPLE 9

Synthesis of $Cu[OCMe(CF_3)CH_2NHCH_2CH=CH_2]_2$

The procedures of Example 1 were followed, using 0.19 g of sodium hydride (7.5 mmol), 0.92 g of the aminoalcohol ligand $HOCMe(CF_3)CH_2NHCH_2CH=CH_2$ (5 mmol) and 0.27 g of $CuCl_2$ (2 mmol). After removing the THF solvent, vacuum sublimation (206 mtorr, 85° C.) gave purple solid $Cu[OCMe(CF_3)CH_2NHCH_2CH=CH_2]_2$. (0.54 g, 1.26 mmol) in 63% yield.

Spectral data of $Cu[OCMe(CF_3)CH_2NHCH_2CH=CH_2]_2$: MS (EI, 70 eV, m/e$^+$, L=$C_7H_{11}F_3NO$), observed (actual) [assignment] {relative intensity}: 427 (427) [CuL$_2$] {0.80}, 358 (358) [CuL$_2$—CF$_3$] {0.20}, 315 (315) [CuL$_2$—C$_3$F$_3$H$_3$O] {1.06},246 (245) [CuL] {8.07}, 182 (182) [L] {3.85}, 70 (70) [L—C$_3$F$_3$H$_3$O] {100}. Anal. Calcd for $C_{14}H_{22}F_6N_2O_2Cu$: C, 39.30; H, 5.18; N, 6.55. Found: C, 39.33; H, 5.40; N, 6.63.

EXAMPLE 10

Synthesis of $Cu[OCMe(CF_3)CH_2NHBu^n]_2$

The procedures of Example 1 were followed, using 0.19 g of sodium hydride (7.5 mmol), 1.0 g of the aminoalcohol ligand $HOCMe(CF_3)CH_2NHBu^n$ (5 mmol) and 0.27 g of $CuCl_2$ (2 mmol). After removing the THF solvent, vacuum sublimation (203 mtorr, 98° C.) gave purple solid $Cu[OCMe(CF_3)CH_2NHBu^n]_2$ (0.76 g, 1.66 mmol) in 83% yield.

Spectral data of $Cu[OCMe(CF_3)CH_2NHBu^n]_2$: MS (EI, 70 eV, m/e$^+$, L=$C_8H_{15}F_3$ NO), observed (actual) [assignment] {relative intensity}: 522 (522) [CuL$_2$+Cu] {1.96},459 (459) [CuL$_2$] {19.06}, 390 (390) [CuL$_2$—CF$_3$] {2.09}, 347 (347) [CuL$_2$—C$_3$F$_3$H$_3$O] {16.79}, 262 (261) [CuL] {100}, 198 (198) [L] {64.04}, 86 (86) [L—C$_3$F$_3$H$_3$O] {64.99}. Anal. Calcd for $C_{16}H_{30}F_6N_2O_2Cu$: C, 41.78; H, 6.57; N, 6.09. Found: C, 42.02; H, 6.52, N, 5.93.

EXAMPLE 11

Synthesis of $Cu[OCMe(CF_3)CH_2NHBu^t]_2$

The procedures of Example 1 were followed, using 0.19 g of sodium hydride (7.5 mmol), 1.0 g of the aminoalcohol ligand $HOCMe(CF_3)CH_2NHBu^t$ (5 mmol) and 0.27 g of $CuCl_2$ (2 mmol). After removing the THF solvent, vacuum sublimation (230 mtorr, 68° C.) gave purple solid $Cu[OCMe(CF_3)CH_2NHBu^t]_2$ (0.65 g, 1.42 mmol) in 71% yield.

Spectral data of $Cu[OC(CF_3)(CH_3)CH_2NHBu^t]_2$: MS (EI, 70 eV, m/e$^+$, L=$C_8H_{15}F_3NO$), observed (actual) [assignment] {relative intensity}: 522 (522) CuL$_2$+Cu] {0.46}, 459 (459) [CuL$_2$] {1.07}, 390 (390) [CuL$_2$—CF$_3$] {0.28}, 347 (347) [CuL$_2$—C$_3$F$_3$H$_3$O] {15.31}, 262 (261) [CuL] {100}, 198 (198) [L] {3.60},86 (86) [L—C$_3$F$_3$H$_3$O] {6.92}. Anal. Calcd for $C_{16}H_{30}F_6N_2O_2Cu$: C, 41.78; H, 6.57; N, 6.09. Found: C, 41.96; H. 6.64; N, 6.04.

EXAMPLE 12

Synthesis of $Cu[OCMe(CF_3)CH_2NHPr^i]_2$

The procedures of Example 1 were followed, using 0.19 g of sodium hydride (7.5 mmol), 0.93 g of the aminoalcohol ligand $HOCMe(CF_3)CH_2NHPr^i$ (5 mmol) and 0.27 g of $CuCl_2$ (2 mmol). After removing the THF solvent, vacuum sublimation (230 mtorr, 81° C.) gave purple solid $Cu[OCMe(CF_3)CH_2NHPr^i]_2$ (0.78 g, 1.82 mmol) in 91% yield.

Spectral data of $Cu[OCMe(CF_3)CH_2NHP^{i}]_2$: MS (EI, 70 eV, m/e$^+$, L=$C_7H_{13}F_3NO$), observed (actual) [assignment] {relative intensity}: 494 (494) [CuL$_2$+Cu] {0.19}, 431 (431) [CuL$_2$] {14.27}, 362 (362) [CuL$_2$—CF$_3$] {1.26}, 319 (319) [CuL$_2$—C$_3$F$_3$H$_3$O] {11.90}, 248 (247) [CuL] {64.49}, 184 (184) [L] {100}, 72 (72) [L—C$_3$F$_3$H$_3$O] {43.43}. Anal. Calcd for $C_{14}H_{26}F_6N_2O_2Cu$: C, 38.93; H, 6.07; N, 6.49. Found: C, 38.92; H, 5.78; N, 6.46.

EXAMPLE 13

Synthesis of $Cu[OCHCF_3CH_2NHCH_2CH_2OMe]_2$

Sodium hydride (0.151 g, 6 mmol) was suspended in 25 mL of THF. To this was added dropwise 0.748 g of the aminoalcohol ligand $HOCHCF_3CH_2NHCH_2CH_2OMe$ (4 mmol) in THF (25 mL). The mixture was stirred at room tepermature for 2 hours until evolution of gas has ceased. After then, the filtrate was transferred into a 100 mL reaction flask containing a suspension of $CuCl_2$ (0.30 g, 2.2 mmol) in THF solution (25 mL). This mixture was stirred at room temperature for 4 hours, giving a purple homogeneous solution alone with an off-white NaCl precipitate. The filtrate was concentrated to dryness, and the residue was purified by vacuum sublimation (230 mtorr, 98° C.), giving 0.583 g of purple complex $Cu[OCHCF_3CH_2NHCH_2CH_2OMe]_2$ (1.34 mmol, 67%).

Spectral data of $Cu[OCHCF_3CH_2NHCH_2CH_2OMe]_2$; MS (EI, 70 eV, m/e$^+$, L=$C_6H_{11}F_3NO_2$), observed (actual) [assignment] {relative intensity}, 498 (498) [CuL$_2$+Cu] {0.32}, 435 (435) [CuL$_2$] {1.91}, 337 (337) [CuL$_2$—CHF$_3$O]{3.80}, 250 (249) [CuL] {100}, 186 (186) [L] {6.68}, 150 (151) [CuL—C$_2$HF$_3$O] {17.86}, 88 (88) [L—C$_2$HF$_3$O] {44.10}. Anal. Calcd for $C_{12}H_{22}F_6N_2O_4Cu$: C, 33.07; H, 5.09; N, 6.43. Found: C, 33.45; H, 5.12; N, 6.59.

EXAMPLE 14

Synthesis of $Cu[OCHCF_3CH_2NHBu^t]_2$

The procedures of Example 13 were followed, using 0.151 g of sodium hydride (6 mmol), 0.74 g of the aminoalcohol ligand $HOCH(CF_3)CH_2NHBu^t$ (4 mmol) and 0.3 g of $CuCl_2$ (2.2 mmol). After removing the THF solvent, vacuum sublimation (228 mtorr, 80° C.) gave purple solid $Cu[OCH(CF_3)CH_2NHBu^t]_2$ (0.62 g, 1.44 mmol) in 72% yield.

Spectral data of Cu[OCHCF₃CH₂NHBu']₂: MS (EI, 70 eV, m/e⁺, L=C₇H₁₃F₃NO), observed (actual) [assignment] {relative intensity}, 494 (494) [CuL₂+Cu] {0.46}, 431 (431) [CuL₂] {0.73}, 333 (333) [CuL₂—C₂HF₃O] {31.11}, 248 (247) [CuL] {100}, 148 (149) [CuL—C₂HF₃O] {37.23}, 86 (86) [L—C₂HF₃O] {36.67}. Anal. Calcd for C₁₄H₂₆F₆N₂O₂Cu: C, 38.93; H, 6.07; N, 6.49. Found: C, 38.92; H, 6.15; N, 6.63.

EXAMPLE 15

Deposition of Copper Metal Thin-Films

Typically, copper metal may be prepared by chemical vapor deposition at about 250–400° C. and about 2000–400 mtorr in a standard cold-wall reactor. Growths of smooth metallic thin films were realized on Si wafers and Pyrex glass. The deposited films were found to be reflective with rood adhesion. The composition of the film was determined by Auger/ESCA analysis. For a Cu thin-film prepared from complex 1 as source reagent, the presence of 96% of copper, along with approximately 1% of carbon, 1% of oxygen and 2% of fluorine were observed. Electrical conductivity measurements give a resistivity in the range 11.8~12.4 μΩ-cm, which is higher than that of bulk copper (1.7 μΩ-cm). This may be attributed to the incorporation of small amounts of carbon, oxygen and fluorine impurities in the Cu films and poor connectivity between grains in the film.

For Cu thin-films deposited using complex 14 as source reagent, a light red and adherent thin-film containing over 99% of Cu metal was obtained. The electrical conductivity 3.4~4.3 μΩ-cm was very close to the physical limit i of the resistivity of bull copper, 1.7 μΩ-cm, suggesting that this source reagent has good potential for real commercial applications. Generally speaking, these experimental results confirm that the lower deposition temperature (250° C.) gives formation of Cu thin-films with greater purity and good resistivity due to the reduced possibility for unwanted ligand decomposition.

While the invention has been particularly shown and described with reference to several embodiments thereof, it will be understood by those skilled in the art that various changes in form and details may be made without departing from the spirit and scope of the invention.

References:
(a) Moshier, R. W.; Sievers, R. E.; Spendlove, L. B. U.S. Pat. No. 3,356,527. (b) Kaloyeros, A. E.; Feng, A.; Garhart, J.; Brooks, K. C.; Ghosh, S. K.; Saxena, A. N.; Luehrs, F. *J. Electrn. Mater.* 1990, 19, 271. (c) Kim, D.-H.; Wentorf, P. H.; Gill, W. N. *J. Electrochem. Soc.* 1993, 140, 3273. (d) Cohen, S. L.; Liehr, M.; Kasi, S. *Appl. Phys. Lett.* 1992, 60, 50. (d) Awaya, N.; *Arita, Y. Jpn. J. Appl. Phys.* 1993, 32, 3915.

²(a) Choi, H.; Hwang, S. *Chem. Mater.* 1998, 10, 2326. (b) Fine, S. M.; Dyer, P. N.; Norman, J. A. T., Muratore, B. A.; Lampietro, R. L. *Mater. Res. Soc. Symp. Proc.* 1990, 204, 415.

³ (a) Noman, J. A. T. et. al. U.S. Pat. No. 5,322,712. (b) Doppelt, P. *Coord. Chem. Rev.* 1998, 178–180, 1785. (c) Naik, M. B.; Gill, W. N.; Wentorf, R. H; Reeves, R. R. *Thin Solid Films* 1995, 262, 60. (d) Donnelly, V. M.; Gross, M. E. *J. Vac. Sci. Technol.*, 1993, 11, 66.

⁴ (a) Chang, I.-S.; Willis, C. J. *Can. J. Chem.* 1977, 55, 2465. (b) Loeb., S. J.; Richardson, J. F.; Willis, C. J. *Inorg. Chem.* 1983, 22, 2736.

⁵ Pinkas, J.; Huffman, J. C.; Baxter, D. V.; Chisholm, M. H.; Caulton, K. G. *Chem. Mater.* 1995, 7, 1589.

⁶ (a) Purdy, A. P.; George, C. F. *ACS Symp. Ser.* 1994, 555, 405. (b) Burton, D. J.; Lu, L. *Top. Curr. Chem.* 1997, 193, 45.

⁷ (a) Goel, S. C.; Kramer, K. S.; Chiang, M. Y.; Buhro, W. E. *Polyhedron* 1990, 9, 611. (b) Goel, S. C.; Buhro, W. E. *Inorg. Synth.* 1997, 31, 294. (c) Young, V. L.; Cox, D. F.; Davis, M. E. *Chem, Mater.* 1993, 5, 1701.

⁸ Yamaguchi, J.; Takeda, T. *Chem. Lett.* 1992, 1933.

⁹ (a) Portis, L. C.; Kulg, J. T.; Mann, K. C.; *J. Org. Chem.* 1974, 39, 3488. (b) Masui, M., Kamada, Y.; Sasaki, E.; Ozaki, S.; *Chem. Pharm. Bull.* 1982, 30,1234.

¹⁰ (a) Nishiyama, T.; Kishi, H.; Kitano, K.; Yamada, F. *Bull. Chem. Soc. Jpn.* 1994, 67, 1765. (b) Ito, K.; Miyajima, S. *J. Heterocycl. Chem.* 1997, 34, 501.

¹¹ Larsen, J.; Jorgensen, K. A. *J. Chem. Soc. Perkn trans.* 2, 1992, 1213.

What is claimed is:

1. A compound of general formula I

$$Cu(OCCF_3R^1CH_2NHR^2)_2 \qquad I$$

wherein R¹ is hydrogen, C1–C4 lower-alkyl, C1–C4 perfluorinated lower-alkyl, and R² is selected from a C1–C6 lower allyl or C1–C6 lower-alkene, which may be substituted by one or more fluorine atoms or by a C1–C6 lower-alkoxy group or by a C1–C6 di-lower-alkylamino group, provided that when R¹ is CF₃, R² is other than methyl.

2. A compound according to claim 1, wherein formula I R¹ is hydrogen, C1–C4 perfluorinated lower-alkyl or C1–C4 lower-alkyl.

3. A compound according to claim 1, wherein formula I R¹ is C1–C4 lower-alkyl.

4. A compound according to claim 1, wherein formula I R¹ is CF₃.

5. A compound according to claim 1, wherein formula I R¹ is hydrogen.

6. A compound according to claim 1, wherein formula I R² is C1–C6 lower-alkyl or C1–C6 lower-alkene, which may be substituted by a C1–C6 lower-alkoxy group or by a C2–C3 di-lower-alkylamino group.

7. A compound according to claim 2, wherein formula I R² is C1–C4 lower-alkyl, substituted by CH₂CH₂NMe₂, CH₂CH₂CH₂NMe₂ or CH₂CH₂NEt₂.

8. A compound according to claim 4, wherein formula I R² is allyl or CH₂CH₂OMe.

9. A compound according to claim 1, wherein formula I R¹ is CF₃ and R² is CH₂CH₂OMe.

10. A compound according to claim 1, wherein formula I R¹ is CF₃ and R² is t-butyl.

11. A compound according to claim 1, wherein formula I R¹ is CF₃ and R² is allyl.

12. A compound according to claim 1, wherein formula I R¹ is CF₃ and R² is n-butyl.

13. A compound according to claim 1, wherein formula I R¹ is CF₃ and R² is iso-butyl.

14. A compound according to claim 1, wherein formula I R¹ is CF₃ and R² is n-propyl.

15. A compound according to claim 1, wherein formula I R¹ is methyl, and R² is CH₂CH₂OMe.

16. A compound according to claim 1, wherein formula I R¹ is methyl, and R² is allyl.

17. A compound according to claim 1, wherein formula I R¹ is methyl, and R² is n-butyl.

18. A compound according to claim 1, wherein formula I R¹ is methyl, and R² is tert-butyl.

19. A compound according to claim 1, wherein formula I R¹ is methyl, and R² is (CH₂)₅Me.

20. A compound according to claim 1, wherein formula I $R^1$ is methyl, and $R^2$ is $CHEt_2$.

21. A compound according to claim 1, wherein formula I $R^1$ is methyl, and $R^2$ is $CMeEt_2$.

22. A compound according to claim 1, wherein formula I $R^1$ is methyl, and $R^2$ is iso-propyl.

23. A compound according to claim 1, wherein formula I $R^1$ is hydrogen, and $R^2$ is n-propyl.

24. A compound according to claim 1, wherein formula I $R^1$ is hydrogen, and $R^2$ is t-butyl.

25. A method of making a compound of formula I, $$Cu(OCCF_3R^1CH_2NHR^2)_2 \qquad I$$

wherein $R^1$ is hydrogen, C1–C4 lower-alkyl, C1–C4 perfluorinated lower-alkyl, and $R^2$ is selected from a C1–C6 lower alkyl or C1–C6 lower-alkene, which may be substituted by one or more fluorine atoms or by a C1–C6 lower-alkoxy group or by a C1–C6 di-alkylamino group, comprising reacting in the presence of a polar organic solvent, a compound of general formula II $$CuX_2 \qquad II$$

wherein X is a halogen selected from Cl, Br and I, with an excess of an alkali metal complex of general formula III $$MOCCF_3R^1CH_2NRH^2 \qquad III$$

wherein M is an alkali metal and $R^2$ is as defined in formula I in claim 1.

26. A method according to claim 25, wherein formula III R1 is hydrogen, C1–C4 perfluorinated lower-alkyl or C1–C4 lower-alkyl.

27. A method according to claim 26, wherein formula III $R^1$ is $CF_3$.

28. A method according to claim 26, wherein formula III $R^1$ is C1–C4 lower-alkyl.

29. A method according to claim 25, wherein formula III $R^2$ is C1–C6 lower-alkyl or C1–C6 lower alkene, which may be substituted by a C1–C6 lower-alkoxy group or by a C2–C3 di-lower-alkylamino group.

30. A method according to claim 26, wherein formula m $R^2$ is C1–C4 lower-alkyl, allyl, $CH_2CH_2OMe$, $CH_2CH_2NMe_2$, $CH_2CH_2CH_2NMe_2$ or $CH_2CH_2NEt_2$.

31. A method according to claim 26, wherein formula III $R^2$ is allyl or $CH_2CH_2OMe$.

32. A method according to claim 25, wherein formula III $R^1$ is $CF_3$ and $R^2$ is $CH_2CH_2OMe$.

33. A method according to claim 25, wherein formula III $R^1$ is $CF_3$ and $R^2$ is t-butyl.

34. A method according to claim 26, wherein M is Li or Na.

35. A method according to claim 34, wherein X is Cl.

36. A method according to claim 35, wherein the solvent is selected from the group consisting of THF, acetone and diethyl ether.

37. A method according to claim 25, wherein the reaction is effected at elevated temperature in the range of 40 to 80° C.

38. A method of plating a substrate with copper metal by vapor deposition, comprising
   (a) providing a compound of general formula I as defined in claim 25,
   (b) volatizing the compound of formula I, to form a copper metal source vapor, and
   (c) contacting the source vapor with a substrate at a temperature of 250–400° C., to deposit copper metal on the substrate.

39. A method according to claim 38, wherein step (b) is carried out in a temperature range of 50–120° C.

40. A method according to claim 39, wherein step (c) is carried out at a temperature in the range of 250–300° C.

41. A method according to claim 40, wherein step (c) the deposition is carried out in the presence of an inert carrier gas.

42. A method according to claim 41, wherein the carrier gas is argon.

43. A method according to claim 42, wherein the substrate is pyrex glass, silicon wafer or titanium nitride thin film.

44. A method according to claim 39, wherein the compound of formula I as defined in claim 19, $R^1$ is $CF_3$ and $R^2$ is $CH_2Ch_2OMe$.

45. A method according to claim 39, wherein the compound of formula I as defined in claim 1, $R^1$ is $CF_3$ and $R^2$ is t-butyl.

* * * * *